US00PP35787P2

(12) United States Plant Patent
Hansen

(10) Patent No.: US PP35,787 P2
(45) Date of Patent: Apr. 30, 2024

(54) ***PHLOX* PLANT NAMED 'PRISMATIC PINK'**

(50) Latin Name: *Phlox paniculata*
Varietal Denomination: Prismatic Pink

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 108 days.

(21) Appl. No.: 18/445,125

(22) Filed: Apr. 17, 2023

(51) Int. Cl.
*A01H 5/02* (2018.01)
*A01H 6/70* (2018.01)

(52) U.S. Cl.
USPC ..... Plt./320

(58) Field of Classification Search
USPC ..... Plt./320
See application file for complete search history.

*Primary Examiner* — Susan McCormick Ewoldt

(57) ABSTRACT

A unique cultivar of Tall *Phlox* plant named 'Prismatic Pink' is characterized by vigorous, dense, upright, highly branched peduncles, with dark-green, lanceolate leaves. Flowering begins in mid-July and continues for up to about six weeks in cooler weather conditions, on heavily-branched peduncles, and completely covers the top of the plant in peak season. Flower petals are bubblegum pink with a dark pink eye. The new plant shows excellent powdery mildew resistance. The new plant is especially suitable for a cut flower, for the landscape as a potted plant, and in the garden as a specimen or en masse.

2 Drawing Sheets

Botanical classification: *Phlox paniculata.*
Variety denomination: 'Prismatic Pink'.

STATEMENT REGARDING PRIOR DISCLOSURES UNDER 37 CFR 1.77(B)(6)

The claimed plant was first sold privately by Walters Gardens, Inc. on May 3, 2022, to Casertano Greenhouses and Farms, Inc. Walters Gardens, Inc. obtained the plant and all information relating thereto, from the inventor. No plants of *Phlox* 'Prismatic Pink' have been sold in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to a new and distinct cultivar of Tall *Phlox* plant known as *Phlox* 'Prismatic Pink' and will be referred to hereafter by its cultivar name, 'Prismatic Pink', or the "new plant". The new plant was hybridized by the inventor in the outdoor trial beds of a wholesale perennial nursery in Zeeland, Michigan on Jul. 27, 2017, as a cross between *Phlox paniculata* 'Dick Weaver' (not patented) as the female or seed parent and the proprietary, unreleased hybrid known only by the breeder code 14-598-1 (not patented) as the male or pollen parent. The new plant passed initial evaluation in the summer of 2019 and was assigned the breeder code 17-16-1 through the remaining evaluation process.

'Prismatic Pink' was first asexually propagated by division in the greenhouses at the same nursery in Zeeland, Michigan in the fall of 2019 with later propagation by cuttings and shoot tip tissue culture. The unique characteristics of the new plant have been found to be reproducible and stable in successive generations by all the above methods of asexually propagated and the resultant plants have been found to be identical to the original selection.

BRIEF SUMMARY OF THE PLANT

*Phlox* 'Prismatic Pink' is unique from all other Tall *Phlox* known to the inventor. The nearest comparison plants known to the inventor include: the female and male parents, 'Glamour Girl' U.S. Plant Pat. No. 25,778, 'Bartwelve' U.S. Plant Pat. No. 11,804, 'Opalescence' U.S. Plant Pat. No. 33,295, and 'Bright Eyes' (not patented).

The female parent has a taller habit, the foliage is narrower, the flowers are more cupped and more lavender-pinkish with fewer flowers per inflorescence. The male parent has wider leaves and the flowers are lighter softer pink.

'Glamour Girl' has flowers that are flowers of hot coral-pink with darker eye. 'Bartwelve' has a smaller habit and smaller inflorescences with fewer flowers that are a different hue. 'Opalescence' has a similar habit with flowers that are light pink with dark pink eyes. 'Bright Eyes' has a taller habit, is more susceptible to powdery mildew, has smaller inflorescences, and the flowers are lighter pink.

*Phlox* 'Prismatic Pink' differs from all other *Phlox* known to the inventor in the following repeatedly observed traits in combination:

1. Vigorous plants of dense upright habit, producing tall, clean, dark-green, glabrous, lanceolate leaves;
2. Multiple lightly-branched stems produce heavily-branched panicles;
3. Flower beginning in mid-July and continuing for up to six weeks, in cool conditions, completely covering the plant at peak flowering;
4. Flowers are bubblegum pink with a dark pink eye;

5. Foliage is highly resistant to powdery mildew in conditions that would normally be exhibited on partially susceptible cultivars.

BRIEF DESCRIPTION OF THE DRAWINGS

The photographs of the new plant demonstrate the unique traits of *Phlox* 'Prismatic Pink' and the overall appearance of the two-year-old plant growing in a full-sun display garden in Zeeland, Michigan. The colors in the drawings are as accurate as reasonably possible with color reproductions. Variations in ambient light spectrum, source, and direction may cause the appearance of minor variations in color.

DETAILED BOTANICAL DESCRIPTION

Figure 1:
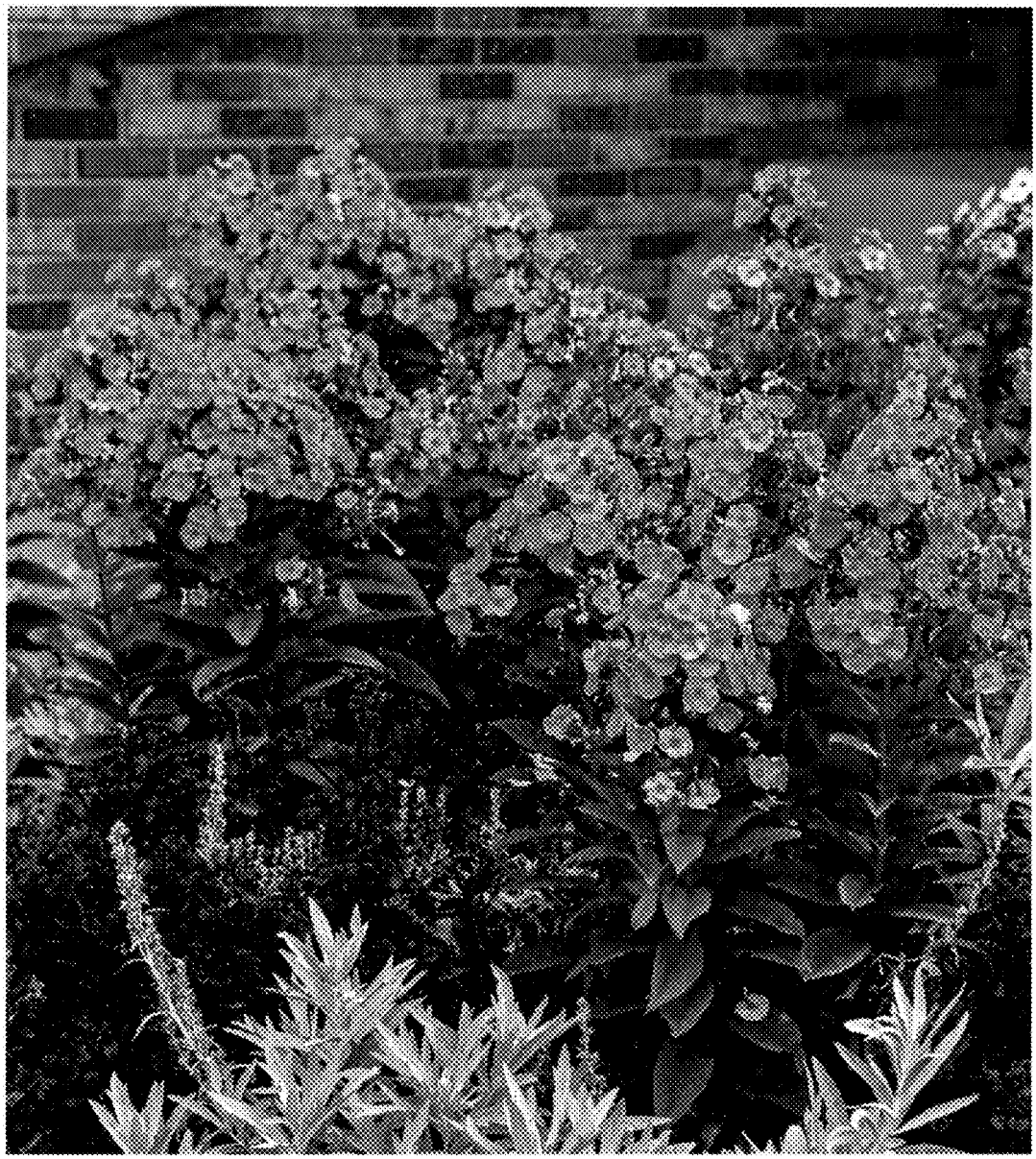
FIG. 1 shows a landscape habit view of the new plant in peak flower.
Figure 2:
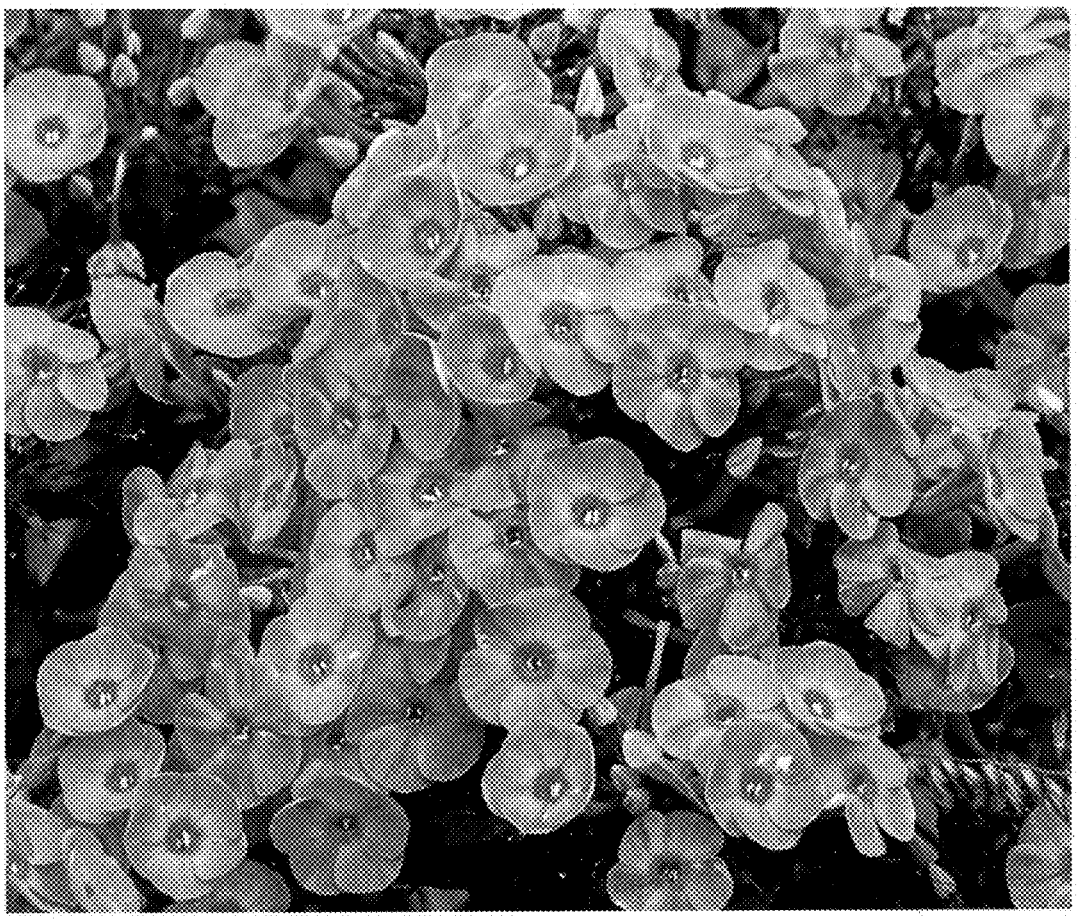
FIG. 2 shows a close-up of the flowers and buds.

The following descriptions and color references are based on the 2015 edition of The Royal Horticultural Society Colour Chart except where common dictionary terms are used. *Phlox* 'Prismatic Pink' has not been observed in all possible environments. The phenotype may vary slightly with different growing environments such as temperature, light, fertility, soil pH, moisture, and maturity levels, but without any change in the genotype. The following observations and size descriptions are based on two-year-old plants in a partially shaded greenhouse or a full-sun trial garden of a wholesale perennial nursery in Zeeland, Michigan with supplemental fertilizer and water as needed.

Botanical classification: *Phlox* hybrid;

Parentage: Female or seed parent is 'Dick Weaver'; male or pollen parent is 14-598-1;

Plant habit: Winter-hardy, evergreen herbaceous perennial; dense, producing about 14 stiff, upright stems; flowering to about 81 cm tall and 62 cm wide;

Propagation: Stem cuttings; rooting in about 3 weeks;

Time to produce a finished crop in 3.8-liter pots: About 8 to 10 weeks; vigorous;

Root: Fibrous and freely branching; color creamy white to tan depending on soil type;

Leaves: Simple; opposite; lanceolate; apex narrowly acute; base attenuate; margin micro-dentate; glabrous adaxial and micro-puberulent abaxial; to about 110 mm long by about 40 mm wide, average about 84 mm long and 32 mm wide;

Leaf color: Adaxial expanding nearest RHS 146B and abaxial nearest RHS 138B and RHS 146D; mature adaxial between RHS 139A and RHS NN137A and mature abaxial between RHS 147B and RHS 147C; lacking anthocyanin expression;

Foliage fragrance: None detected;

Veins: Pinnate; convergent near leaf margin; glabrous adaxial and abaxial, midrib about 1.5 mm wide at base; slightly impressed adaxial and costate abaxial;

Vein color: Adaxial midrib and primary veins nearest RHS 146B; abaxial midrib nearest RHS 145C, and primary and secondary veins nearest RHS 146A;

Petiole: Flattened; glabrous adaxial and abaxial; about 2 mm long and 2 mm wide;

Petiole color: Nearest RHS 146C adaxial and nearest RHS 145C abaxial;

Stems: Cylindrical; stiff; upright; glabrescent, to puberulent distally; branching below flowers; to about 79 cm long and 13 mm diameter near base, average about 72 cm long and 11 mm diameter at base;

Stem color: Proximal portion RHS 146B with slightly-raised longitudinal striations of nearest; distal portion nearest RHS 146B; lacking anthocyanin expression;

Nodes: 20 nodes before flowers; average about 2.2 cm apart, greater proximally;

Node color: Color nearest RHS 146C;

Inflorescence: Upright; with 16 distally branched nodes; densely flowering in about the upper 20 cm and about 21 cm wide; about 400 to 700 flowers per branched stem;

Flowers: Perfect; salverform; mostly flat faced; to about 30 mm across face and 24 mm tall; with fused corolla tube about 22 mm long and 4 mm diameter near face and 2.0 mm diameter at base; attitude upright to outwardly;

Flower longevity: About 5 days on plant; self-cleaning;

Flowering season: Beginning in mid-July for up to about six weeks;

Flower fragrance: Lightly sweet;

Buds one to two days prior to opening: Narrowly clavate; acute apex with rounded base; petals implicate; abaxial corolla tube puberulent, bulb and calyx glabrous;

Bud size: About 25 mm long, bulb to about 8.5 mm long and 6 mm diameter near middle; corolla tube portion to about 17 mm long and 4 mm diameter below bulb and proximal bulb and base of corolla about 2 mm diameter;

Bud color: Exposed petal bulb portion between RHS 76C and RHS 76D with fine blotches nearest RHS 77C; corolla tube portion between RHS N77B and RHS N79B; calyx nearest RHS 147B with white translucent margins nearest RHS NN155D and moderate anthocyanin blushing of nearest RHS N79B;

Petals: Typically five; consisting of limb and basal claw fused into corolla tube; limb obdeltoid; apex rounded, margin entire; limbs imbricate about 30 percent; limb glabrous adaxial and abaxial, adaxial corolla tube pubescent in proximal 4 to 6 mm and glabrous distally, abaxial corolla tube puberulent;

Petal size: Limb about 12 mm long and 18 mm wide near middle; tube about 22 mm long and 4 mm diameter near face and 3 mm diameter near base;

Petal color upon first opening:

*Adaxial*.—Limb between RHS 70B and RHS 72C, with center eye nearest RHS NN74A; distal 14 mm of corolla tube between RHS 70B and RHS 70C, proximal 6 mm of corolla tube portion nearest RHS 145D.

*Abaxial*.—Limb between RHS NN74D and RHS 75D, corolla tube basal 2 mm nearest RHS 145D, distally between RHS 63A and RHS 63B.

Petal color upon maturity:

*Adaxial*.—Limb between RHS 77C and RHS N74C, with center eye nearest RHS N74A; distal 14 mm of corolla tube between RHS 77B and RHS 75BD, proximal 6 mm of corolla tube portion nearest RHS 155D.

*Abaxial*.—Limb nearest RHS 76B, distal corolla tube between RHS 77B and RHS N77B.

Androecium: Five;

*Filaments*.—Five, adnate to inner corolla to various heights about 12.0 mm to 2.0 mm from base; free in the distal 1 mm and 0.2 mm in diameter.

*Filament color*.—In free portion nearest RHS NN155D, where fused nearest RHS 77D.

*Anther*.—Five; oblong ellipsoidal; dorsifixed; longitudinal; about 3 mm long by 1 mm wide; color nearest RHS 11D.

*Pollen*.—Nearly microscopic; color nearest RHS 18C.

Gynoecium: One pistil per flower; 23 mm long;

*Style*.—Cylindrical; about 21 mm long and 0.3 mm diameter when flower is mature; persistent after flower abscission; color nearest RHS N77B.

*Stigma*.—Typically trifid in proximal 1 mm long; about 0.3 mm diameter; color nearest RHS 1C.

*Ovary*.—Superior; turbinate; glabrous; lustrous; acute apex and truncate base; about 3 mm long and 1.2 mm diameter at base; color nearest RHS 143A.

Calyx: Campanulate; to about 8 mm long and 4 mm across at apex;

Sepals: Five; linear; adaxial and abaxial slightly lustrous; narrowly acute apex, fused in basal 4 mm, free in distal 4 mm; margin entire; individually about 8 mm long and 1.5 mm wide at fusion;

Sepal color: Adaxial and abaxial distally nearest RHS 147B with transparent to translucent margin about 0.5 mm wide lightly blushed nearest RHS N77B, adaxial and abaxial proximally nearest RHS 147C;

Peduncle: Glabrous; stiff; upright; cylindrical; highly branched; to 30 cm long and 8 mm diameter below branches; with up to 16 branches at about a 40-degree angle above horizontal, branches to about 2.5 mm diameter at base and 20 cm long;

Peduncle color: Nearest RHS 146C;

Pedicel: Cylindrical; micro-puberulent; flexible; upright to outwardly; arcuate slightly upwardly on outer flowers, straight on inner flowers; to about 5 mm long and 1 mm diameter;

Pedicel color: Between RHS 145A and RHS 146D on ventral side, nearest RHS 146C with light blush of nearest RHS N186C;

Fruit: Rare; dehiscent, few-seeded capsule, typically 1 seed; fecundity low; flattened ellipsoidal; glabrous; ellipsoidal; apex acute; base rounded; to about 6 mm long and 4 mm diameter in middle; color at maturity nearest RHS 165B;

Seeds: Very rare; flattened ellipsoidal; glabrous; to 4 mm long, 2 mm across and 1.5 mm thick; color between RHS N199A and RHS N200A;

Hardiness and culture: The new plant grows best with full sun, light moisture and deep drainage; hardy to at least from USDA zone 3 through 8.

Disease and pest resistance: *Phlox* 'Prismatic Pink' demonstrates excellent powdery mildew resistance from various species in the order Erysiphales under conditions that would normally show symptoms. No pest resistance beyond that common for *Phlox* has been observed.

I claim:

1. A new and distinct cultivar of Tall *Phlox, Phlox* plant named 'Prismatic Pink', as herein described and illustrated.

* * * * *